United States Patent
Wu

(10) Patent No.: US 11,369,520 B2
(45) Date of Patent: Jun. 28, 2022

(54) AUTO-DARKENING WELDING HELMET

(71) Applicant: Tecmen Electronics Co., Ltd., Jiangsu (CN)

(72) Inventor: Ziqian Wu, Nanjing (CN)

(73) Assignee: Tecmen Electronics Co., Ltd., Nanjing (CN)

( * ) Notice: Subject to any disclaimer, the term of this patent is extended or adjusted under 35 U.S.C. 154(b) by 89 days.

(21) Appl. No.: 16/615,781

(22) PCT Filed: Aug. 12, 2019

(86) PCT No.: PCT/CN2019/100207
§ 371 (c)(1),
(2) Date: Nov. 21, 2019

(87) PCT Pub. No.: WO2020/082859
PCT Pub. Date: Apr. 30, 2020

(65) Prior Publication Data
US 2020/0368067 A1  Nov. 26, 2020

(30) Foreign Application Priority Data

Oct. 23, 2018  (CN) .......................... 201811281541.0
Oct. 23, 2018  (CN) .......................... 201821722015.9

(51) Int. Cl.
*A61F 9/06* (2006.01)
*A42B 3/04* (2006.01)

(52) U.S. Cl.
CPC .............. *A61F 9/067* (2013.01); *A42B 3/044* (2013.01)

(58) Field of Classification Search
CPC ................................ A61F 9/067; A42B 3/044
See application file for complete search history.

(56) References Cited

U.S. PATENT DOCUMENTS

| 3,227,866 | A  | 1/1966 | Peters et al. |
| 6,884,987 | B2 | 4/2005 | Hamilton et al. |
| 7,934,846 | B1 | 5/2011 | Schwanz |
| 9,629,752 | B1 | 4/2017 | Graham |
| 2005/0077278 | A1 | 4/2005 | Steinemann |

(Continued)

FOREIGN PATENT DOCUMENTS

| CN | 203169416 U | 9/2013 |
| CN | 207755452 U | 8/2018 |

(Continued)

OTHER PUBLICATIONS

International Search Report and Written Opinion regarding International Application No. PCT/CN2019/100207, dated Nov. 18, 2019, 10 pages.

(Continued)

*Primary Examiner* — Thomas M Sember

(57) ABSTRACT

An auto-darkening welding helmet comprises a helmet casing; an auto-darkening filter installed in the helmet casing; and a lighting device installed in the helmet casing, wherein the auto-darkening filter includes a liquid crystal panel which is switchable between a non-opaque state and an opaque state, wherein the lighting device comprises a cable connectable to the auto-darkening filter such that when the liquid crystal panel is in the non-opaque state the lighting device automatically emits light towards a front of the liquid crystal panel and when the liquid crystal panel is in the opaque state the lighting device does not automatically emit light.

20 Claims, 5 Drawing Sheets

(56) References Cited

U.S. PATENT DOCUMENTS

| | | |
|---|---|---|
| 2012/0180180 A1 | 7/2012 | Steve et al. |
| 2017/0252215 A1 | 9/2017 | Wu |
| 2017/0258639 A1 | 9/2017 | Wu |
| 2017/0290707 A1 | 10/2017 | Wu |
| 2018/0271709 A1 | 9/2018 | Currie |
| 2019/0310503 A1 | 10/2019 | Wu |

FOREIGN PATENT DOCUMENTS

| | | |
|---|---|---|
| CN | 109745173 A | 5/2019 |
| EP | 3228287 A1 | 10/2017 |
| JP | S42-14754 Y1 | 8/1967 |
| JP | 2001-174763 A | 6/2001 |

OTHER PUBLICATIONS

IP Australia, Examination report No. 1 for standard patent application, dated Mar. 11, 2021 regarding Application No. 2019367425, 5 pages.
IP Australia, Examination report No. 3 for standard patent application dated Jul. 13, 2021, regarding Application No. 2019367425, 4 pages.
Extended European Search Report dated Oct. 11, 2021 regarding Application No. 19875803.9, 8 pages.
Japanese Patent Office Notice of Reasons for Refusal dated Oct. 12, 2021 regarding Application No. 2020-552283, 9 pages.

AUTO-DARKENING WELDING HELMET

CROSS-REFERENCE TO RELATED APPLICATIONS

This application is a 371 National Stage of International Application No. PCT/CN2019/100207 filed Aug. 12, 2019, which claims priority to Chinese Patent Application No. 201811281541.0, filed Oct. 23, 2018, and Chinese Patent Application No. 201821722015.9, filed Oct. 23, 2018, the disclosures of which are herein incorporated by reference in their entirety.

BACKGROUND

1. Field

The present disclosure generally relates to an auto-darkening welding helmet, especially with a lighting device.

2. Description of Related Art

In order to protect eyes of operators in the site of welding, auto-darkening welding helmets are more and more commonly used. In some dark and small spaces, it is sometimes difficult for an operator who had worn a welding helmet on his/her head to remove the welding helmet. In the meanwhile, in order to watch a location of a workpiece to be welded, the operator shall turn on a lighting device carried on him/her. Prior to initiation of arc-welding, he/she shall turn off the lighting device. If a test for welding is needed, turning on/off the lighting device will be very frequent.

Besides, in the site of welding, the operator shall let one hand of him/her operate and hold the lighting device, which may result in great inconvenience in case of the small spaces.

SUMMARY

In order to solve those issues, the present disclosure is aimed at proposing an improved auto-darkening welding helmet such that an operator can carry out welding work in a dark and small space with observing the welding state conveniently and clearly.

In one aspect of the present disclosure, an auto-darkening welding helmet is provided, comprising: a helmet casing; an auto-darkening filter installed in the helmet casing and including a liquid crystal panel switchable between a non-opaque state and an opaque state; a lighting device installed in the helmet casing, wherein the lighting device comprises a cable for being connected to the auto-darkening filter such that when the liquid crystal panel is in the non-opaque state the lighting device automatically emits light towards a front of the liquid crystal panel and when the liquid crystal panel is in the opaque state the lighting device does not automatically emit light.

Optionally, the lighting device is releasably installed in the helmet casing above or laterally aside the auto-darkening filter.

Optionally, the lighting device comprises a light-emitting diode (LED) lamp for emitting light.

Optionally, the lighting device is provided with a button to directly control the LED lamp to be powered on or off.

Optionally, the auto-darkening filter comprises a control circuit which controls the LED lamp to selectively emit light or not whether the LED lamp is powered on.

Optionally, the lighting device comprises a battery for powering the LED lamp.

Optionally, the lighting device is able to share a battery of the auto-darkening filter.

Optionally, the auto-darkening filter comprises an optical sensor for receiving an arc-light signal, wherein depending on existence of the arc-light signal, the control circuit determines whether the liquid crystal panel is in the non-opaque or opaque state and whether the LED lamp emits light or not.

Optionally, the LED lamp is controlled by the button independently of the control circuit.

According to the technical means of the present disclosure, in the dark and small space, every time arc-welding is initiated, when the auto-darkening filter takes effect, the lighting device is automatically powered off and when the auto-darkening filter does not take effect, the lighting device is automatically powered on. Therefore, the operator can watch the welding result conveniently and clearly without the helmet being removed at a silence prior to performing a welding operation at a location. This will greatly improve work efficiency.

BRIEF DESCRIPTION OF THE DRAWINGS

The fore and other aspects of the present disclosure will be well understood by the following description in combination with the attached drawings. It should be understood that although the drawings may be given in differential ratios, understanding to the present disclosure is not affected. In the drawings.

DETAILED DESCRIPTION

Figure 1:
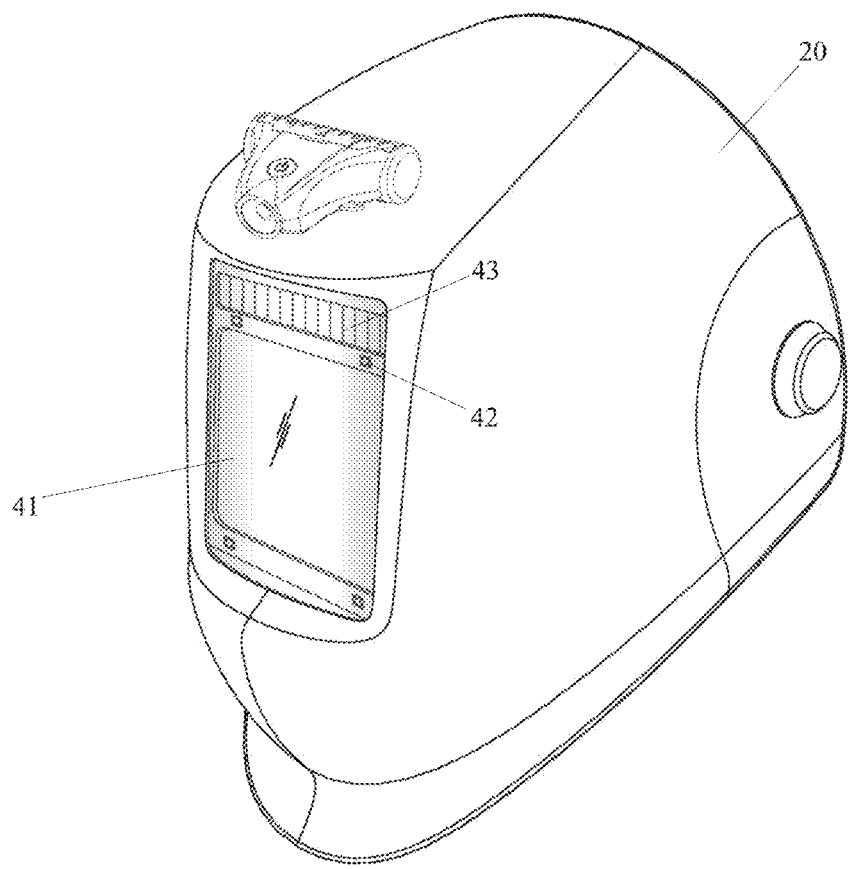
FIG. 1 is a perspective view schematically illustrating an auto-darkening welding helmet according to an embodiment of the present disclosure.

In the drawings of the present disclosure, features having similar or identical configurations or functions are represented by the same reference numerals.

Figure 2:
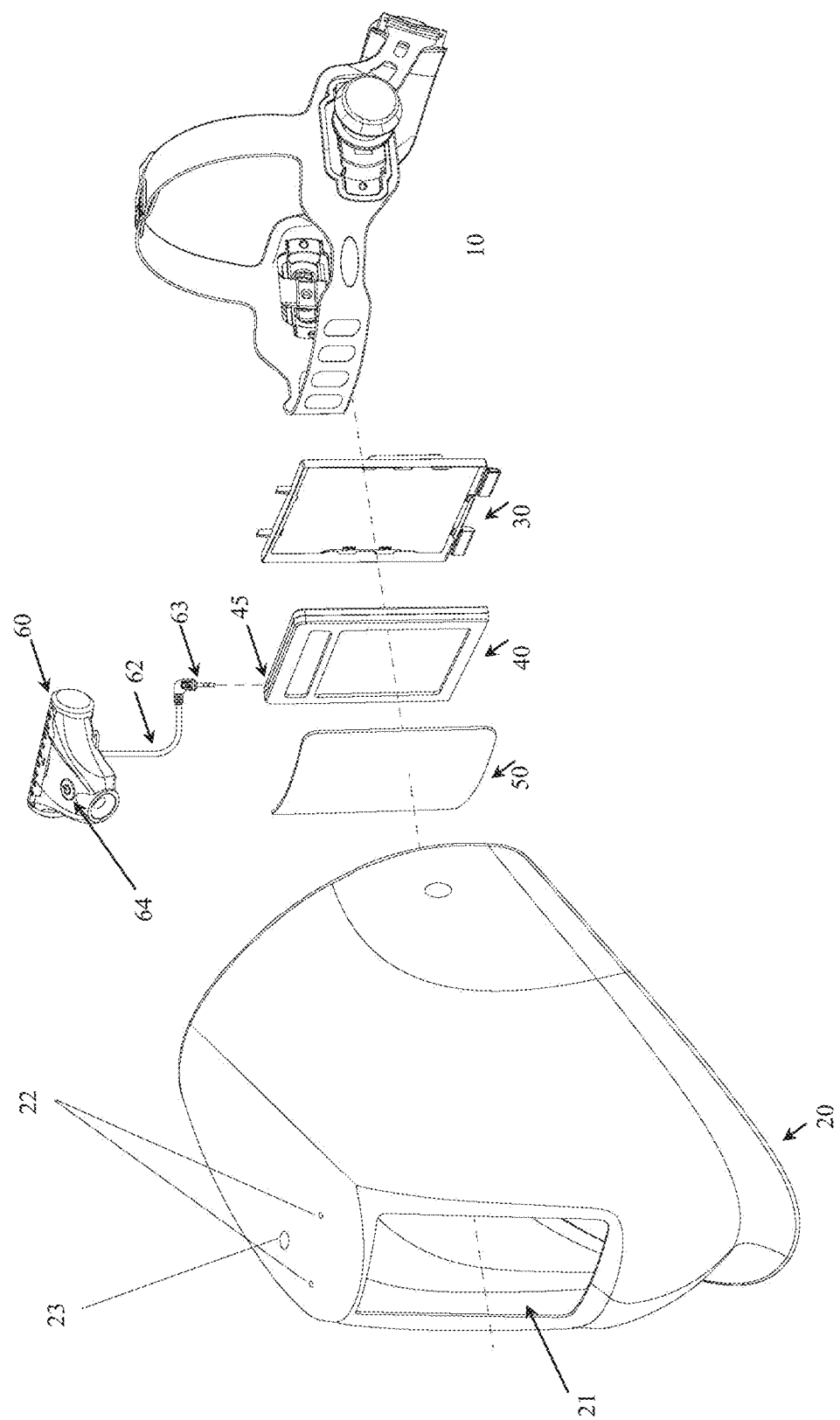
FIG. 2 is an exploded view schematically illustrating the auto-darkening welding helmet of FIG. 1.
Figure 3:
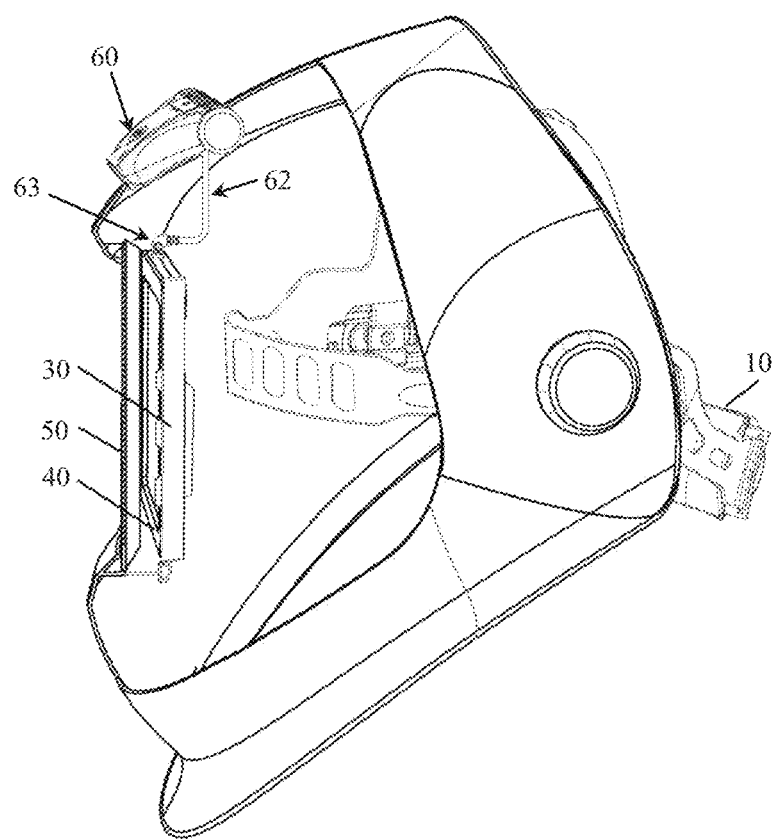
FIG. 3 is a partially cross-sectional view schematically illustrating the auto-darkening welding helmet of FIG. 1.

FIG. 1 schematically illustrates an embodiment of an auto-darkening welding helmet 100 according to the present disclosure, and FIG. 2 schematically shows an exploded view of the auto-darkening welding helmet 100.

As shown, the auto-darkening welding helmet 100 comprises a headgear 10 and a helmet casing 20 releasably installed on the headgear 10. For instance, the helmet casing 20 is made of a synthetic fiber material, for example nylon. The helmet casing 20 is shaped to adapt to the contour of an ordinary adult's head. The headgear 10 is used to be worn on an operator's head within the helmet casing 20. It should be noted that in the context of the present disclosure, the term "within" when used with the auto-darkening welding helmet or its constituent part(s) means a direction of the auto-darkening welding helmet or its constituent part(s) towards the operator's head when the auto-darkening welding helmet or its constituent part(s) is worn; the term "outside" when used with the auto-darkening welding helmet or its constituent part(s) means a direction of the auto-darkening welding helmet or its constituent part(s) away from the operator's head when the auto-darkening welding helmet or its constituent part(s) is worn.

The helmet casing 20 is pivotally installed in the headgear 10, such that when the auto-darkening welding helmet 100 is worn in place, the helmet casing 20 may shield the entire face of the operator. A substantially rectangular opening 21 is formed in the helmet casing 20. A retainer 30 is releasably installed in the opening 21. An auto-darkening filter 40 is releasably installed in the retainer 30.

The auto-darkening filter 40 generally comprises a liquid crystal panel 41. Under control of a control circuit 44 of the auto-darkening filter 40, the liquid crystal panel 41 is usually in a non-opaque state. However, it can become in an opaque state at the moment that arc-welding is initiated such that the operator's eyes can be protected from any damageable rays. The auto-darkening filter 40 is provided with an optical sensor 42 on an outer side so as to, at the moment that the arc-welding is initiated, receive an arc-light signal and notify the control circuit 44 to operate the liquid crystal panel 41. A photoelectric converter 43 is also provided on the outer side of the auto-darkening filter 40 to convert the high-intensive arc-light, during initiation of the arc-welding, into electric energy which is then stored in a (not-shown) battery of the auto-darkening filter 40 for later use. Especially, on the outside of the auto-darkening filter 40, a transparent protective sheet 50 is releasably provided in the opening 21 so as to prevent any splashing matters from striking the liquid crystal panel 41.

The auto-darkening welding helmet 100 also comprises a lighting device 60. The lighting device 60 for example comprises a housing, and a lamp (especially a LED lamp) and a battery which are installed in the housing. The lighting device 60 is for example installed at the top of the helmet casing 20, such that when the auto-darkening welding helmet 100 is worn in place, the lamp of the lighting device 60 can face towards a direction in front of the operator, and when the lighting device is powered on, the lamp can emit light which reaches a certain distance in front of the helmet casing 20. For instance, two mounting holes 22 are provided at the top of the helmet casing 20. Two holes 61 are also provided in the housing of the lighting device 60. In this way, by aligning the holes 61 of the lighting device 60 with the mounting holes 22 of the helmet casing 20 respectively, inserting bolts through them and fastening the bolts with nuts, the lighting device 60 can be secured to the helmet casing 20. It should be understood by one ordinary person in the art that the lighting device 60 can be disposed in any other location of the helmet casing 20 where light for illumination can be provided in front of the operator. For instance, optionally, the lighting device 60 can be disposed laterally aside the opening 21 of the helmet casing 20 such that when the auto-darkening welding helmet 100 is worn in place, the lamp can be directed towards in front of the operator. Furthermore, the lighting device 60 can be connected to the helmet casing 20 in a similar manner by which a releasable flash lamp for example in a camera field is connected to a digital camera or a Digital Single Lens Reflex.

A control circuit is also provided in the lighting device 60 to control switching on/off of the lamp. The lighting device 60 also comprises a button 64 to directly control the lamp of the lighting device 60 such that it can be powered on/off. A cable 62 is connected to the control circuit and is provided with an electric terminal 63. As shown by FIG. 2, a through-hole 23 is formed in the helmet casing 20 such that when the lighting device 60 is installed in the helmet casing 20, the cable 62 and its electric terminal 63 can pass through the hole 23.

A receptacle 45 is provided in the auto-darkening filter 40 to receive the electric terminal 63. Using the cable 62, the control circuit 44 of the auto-darkening filter 40 can be connected to the control circuit 44 of the lighting device 60, and the former can be used to independently control operation of the lighting device 60, for example switch on or off the lamp, when the button 64 has been pressed to power on the lamp of the lighting device 60.

Figure 4:
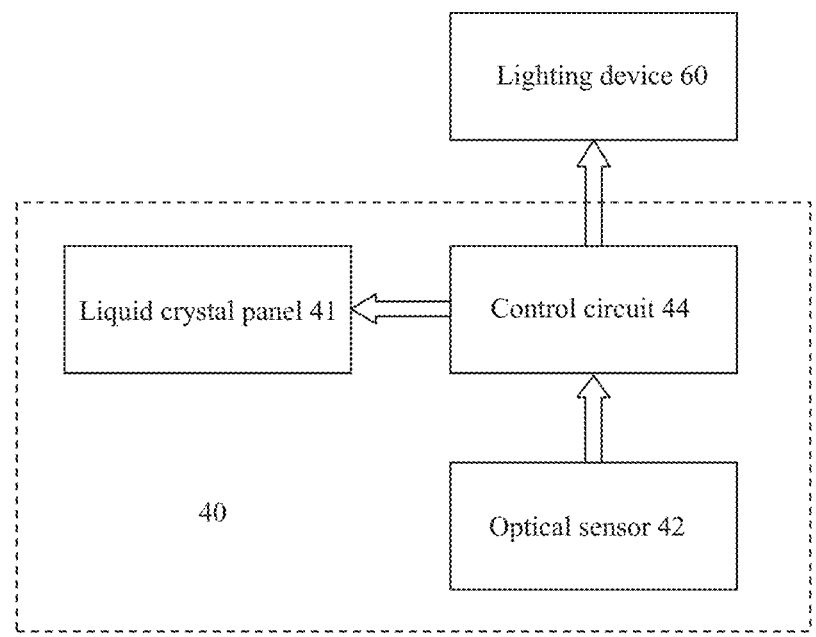
FIG. 4 is a block diagram schematically illustrating how to control the auto-darkening welding helmet according to the present disclosure.
Figure 5:
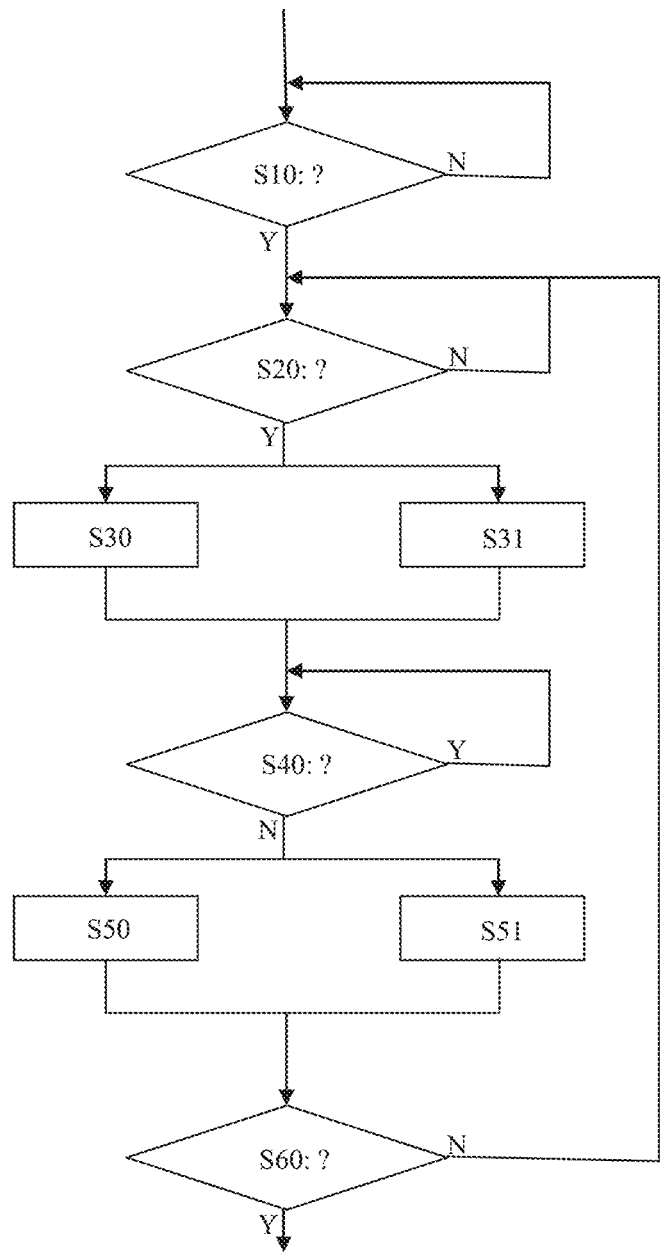
FIG. 5 illustrates an example method of the control process according to the present disclosure.

FIG. 4 simply illustrates a block diagram for controlling the auto-darkening filter 40. It can be seen that the control circuit 44 of the auto-darkening filter 40 can receive from the optical sensor 42 the arc-light signal and, depending on it, send to the liquid crystal panel 41 instructions for activating or de-activating the same and at the same time send to the lighting device 60 instructions for activating or de-activating the same. A set of instructions are stored in the control circuit 44 of the auto-darkening filter 40 to implement a control process. Now, an example of the control process according to the present disclosure will be illustratively explained by referring to FIG. 5 below.

First, at step S10, it is judged whether the button 64 of the lighting device 60 is pressed to enable the lamp of the lighting device 60 to emit light. If the judgement result is "NO", the process continues to wait. If the judgement result is "YES", the process goes to step S20. At step S20, it is determined whether the arc-light signal is generated. For example, this can be achieved by the control circuit 44 of the auto-darkening filter 40 determining whether the arc-light signal exists from the optical sensor 42. If the determination result is "NO", the process continues to wait. If the determination result is "YES", the process goes to step S30. At step S30, the liquid crystal panel 41 is activated. That is, the liquid crystal panel 41 is changed from a non-opaque state to an opaque state. In the meanwhile, at step S31, the lamp of the lighting device 60 is enabled not to emit light. Then, at step S40, it is determined whether the arc-light signal exists. If the determination result is "YES", the current state is upheld and the process continues to wait. If the determination result is "NO", the process goes to step S50. At step S50, the liquid crystal panel 41 is deactivated. That is, the liquid crystal panel 41 is changed from the opaque state to the non-opaque state. In the meanwhile, at step S51, the lamp of the lighting device 60 is enabled to emit light again. Then, at step S60, it is determined whether the button 64 of the lighting device 60 is pressed. If the determination result is "NO", the process goes to step S20. If the determination result is "YES", the process can stop.

Using the process according to the present disclosure, when the button 64 of the lighting device 60 is first pressed to enable the lamp to emit light, the liquid crystal panel 41 is always activated, every time initiation of arc-welding, to protect the operator's eyes and, at the same time, the lamp of the lighting device 60 can be automatically switched off. Then, when no arc-welding is initiated, the liquid crystal panel 41 can be automatically deactivated and the lamp is automatically switched on. Therefore, it will be convenient for the operator to observe how a workpiece is welded at any time during its welding.

In an alternative embodiment, the step S40 can be provided such that only when the determination result is "NO" and the result is the same after a period (such as one second) is waited for, the process goes to step S50 and step S51. In an alternative embodiment, the button 64 of the lighting device 60 can be configured such that when the lighting device 60 is being operated by the control circuit 44 of the auto-darkening filter 40, such operation can be terminated directly by the button 64 of the lighting device 60 and the lighting device 60 can be switched on/off by the same.

Although the lighting device 60 is provided with the battery in the illustrated embodiments, the lighting device 60 can alternatively share the battery of the auto-darkening filter 40. Furthermore, in an alternative embodiment, the button 64 of the lighting device 60 can be dispensed with and the lighting device 60 can be configured such that as soon as the electric terminal 63 is inserted into the receptacle 45 of the auto-darkening filter 40, the control circuit 44 of the auto-darkening filter 40 will automatically enable the lamp of the lighting device 60 to be powered on to emit light and when the electric terminal 63 is removed, the lamp is powered off, and thus the steps S10 and S60 are omitted in the process.

In the context of the present disclosure, various embodiments can be arbitrarily combined with each other. Although some specific embodiments are described here, they are given out for illustrative purposes only and cannot be deemed to constrain the scope of the present disclosure. Without departing from the spirit and scope of the present disclosure, various replacements, alternations and modifications can be thought out.

The invention claimed is:

1. An auto-darkening welding helmet, comprising:
   a helmet casing;
   an auto-darkening filter installed in the helmet casing and including a liquid crystal panel configured to be switched between a non-opaque state and an opaque state; and
   a lighting device releasably installed in the helmet casing above or laterally aside the auto-darkening filter, the lighting device comprising a cable configured to be connected to the auto-darkening filter in a manner that:
      when the liquid crystal panel is in the non-opaque state, the lighting device automatically emits light towards a front of the liquid crystal panel, and
      when the liquid crystal panel is in the opaque state, the lighting device does not automatically emit light.

2. The auto-darkening welding helmet of claim 1, wherein the lighting device comprises an LED lamp configured to emit light.

3. The auto-darkening welding helmet of claim 2, wherein the lighting device includes a button configured to control the LED lamp to be powered on or off.

4. The auto-darkening welding helmet of claim 3, wherein the auto-darkening filter comprises a control circuit configured to control the LED lamp to emit light based on the LED lamp being powered on.

5. The auto-darkening welding helmet of claim 4, wherein the lighting device comprises a battery to power the LED lamp.

6. The auto-darkening welding helmet of claim 4, wherein the lighting device comprises a battery configured to power the lighting device and the auto-darkening filter.

7. The auto-darkening welding helmet of claim 4, wherein:
   the auto-darkening filter comprises an optical sensor configured to receive an arc-light signal;
   based on the optical sensor receiving the arc-light signal, the control circuit is configured to determine the liquid crystal panel is in the opaque state and control the LED lamp to not emit light; and
   based on the optical sensor not receiving the arc-light signal, the control circuit is configured to determine the liquid crystal panel is in the non-opaque state and control the LED lamp to emit light.

8. The auto-darkening welding helmet of claim 7, wherein the button is configured to control the LED lamp independently of the control circuit.

9. The auto-darkening welding helmet of claim 2, wherein the auto-darkening filter comprises a control circuit configured to control the LED lamp to emit light based on the LED lamp being powered on.

10. The auto-darkening welding helmet of claim 9, wherein the lighting device comprises a battery to power the LED lamp.

11. The auto-darkening welding helmet as recited in claim 9, wherein the lighting device comprises a battery configured to power the lighting device and the auto-darkening filter.

12. The auto-darkening welding helmet of claim 9, wherein:
   the auto-darkening filter comprises an optical sensor configured to receive an arc-light signal;
   based on the optical sensor receiving the arc-light signal, the control circuit is configured to determine the liquid crystal panel is in the opaque state and control the LED lamp to not emit light; and
   based on the optical sensor not receiving the arc-light signal, the control circuit is configured to determine the liquid crystal panel is in the non-opaque state and control the LED lamp to emit light.

13. The auto-darkening welding helmet of claim 12, wherein the lighting device includes a button configured to control the LED lamp to be powered on or off.

14. The auto-darkening welding helmet of claim 12, wherein the lighting device comprises an LED lamp configured to emit light.

15. The auto-darkening welding helmet of claim 14, wherein the lighting device includes a button configured to control the LED lamp to be powered on or off.

16. The auto-darkening welding helmet of claim 15, wherein the auto-darkening filter comprises a control circuit configured to control the LED lamp to emit light based on the LED lamp being powered on.

17. The auto-darkening welding helmet of claim 16, wherein the lighting device comprises a battery to power the LED lamp.

18. The auto-darkening welding helmet as recited in claim 16, wherein the lighting device comprises a battery configured to power the lighting device and the auto-darkening filter.

19. The auto-darkening welding helmet of claim 16, wherein the auto-darkening filter comprises an optical sensor configured to receive an arc-light signal;
   based on the optical sensor receiving the arc-light signal, the control circuit is configured to determine the liquid crystal panel is in the opaque state and control the LED lamp to not emit light; and
   based on the optical sensor not receiving the arc-light signal, the control circuit is configured to determine the liquid crystal panel is in the non-opaque state and control the LED lamp to emit light.

20. The auto-darkening welding helmet of claim 1, wherein the cable passes through the helmet casing to be connected to the auto-darkening filter.

* * * * *